US00PP23497P3

(12) United States Plant Patent

Clark et al.

(10) Patent No.: US PP23,497 P3

(45) Date of Patent: Mar. 26, 2013

(54) BLACKBERRY PLANT NAMED 'REUBEN'

(50) Latin Name: *Rubus subgenus Eubatus* sect. *Moriferi & Ursini* hybrid
Varietal Denomination: Reuben

(75) Inventors: John Reuben Clark, Fayetteville, AR (US); Jane Fairlie, Spalding (GB)

(73) Assignee: Hargreaves Plants Ltd, Spalding, Lincs (GB)

( * ) Notice: Subject to any disclaimer, the term of this patent is extended or adjusted under 35 U.S.C. 154(b) by 0 days.

(21) Appl. No.: 12/928,424

(22) Filed: Dec. 10, 2010

(65) Prior Publication Data

US 2012/0151645 P1 Jun. 14, 2012

(51) Int. Cl.
*A01H 5/00* (2006.01)

(52) U.S. Cl. ..... Plt./203

(58) Field of Classification Search ..... Plt./203
See application file for complete search history.

*Primary Examiner* — Kent L Bell

(74) *Attorney, Agent, or Firm* — Jondle & Associates, P.C.

(57) ABSTRACT

This invention relates to a new and distinct variety of blackberry plant named 'Reuben', which is primarily characterized by its primocane fruiting habit, large fruit size, high quality, and high productivity, is disclosed.

4 Drawing Sheets

Genus and species: *Rubus* subgenus *Eubatus* sect. *Moriferi & Ursini* hybrid.

Variety denomination: 'Reuben'.

BACKGROUND OF THE NEW PLANT

The present invention relates to a new and distinct blackberry variety designated 'Reuben' and botanically known as *Rubus* subgenus *Eubatus* sect. *Moriferi & Ursini*. This new Blackberry variety was discovered in 2005 in Fayetteville, Ark., and originated from a hand pollinated cross between the female parent blackberry plant 'A-2292T' (unpatented) and the male parent blackberry plant 'APF-44' (unpatented). Seeds from this cross were shipped to Spalding, Lincs, United Kingdom, in November of 2005, where the seeds were germinated. In summer 2006, the seeds were field planted and, in late autumn 2006, one seedling, designated HPB3 ('Reuben'), was selected for its primocane fruiting habit, large fruit size, high quality, and high productivity.

The new variety 'Reuben' was first propagated via root cuttings and was subsequently propagated via root cuttings in February 2009 in Spalding, Lincs, United Kingdom. 'Reuben' has been asexually reproduced by root cuttings and in-vitro propagation for 2 generations. The present invention has been found to be stable and reproduce true to type through successive asexual propagations via root cuttings.

PLANT BREEDER'S RIGHTS

Plant Breeder's Rights for this variety were applied for in the European Union on Dec. 14, 2009. 'Reuben' has not been made sold or made publicly available more than one year prior to the filing date of this application.

SUMMARY OF THE INVENTION

The following are the most outstanding and distinguishing characteristics of this new variety when grown under normal horticultural practices in Spalding, Lincs, United Kingdom.

1. A primocane fruiting habit;
2. Large fruit size;

3. High quality; and
4. High productivity.

DESCRIPTION OF THE PHOTOGRAPHS

This new Blackberry plant is illustrated by the accompanying photographs, which show the fruit of the plant as well as the canes. The colors shown are as true as can be reasonably obtained by conventional photographic procedures. The photographs are of two-year-old plants.

DESCRIPTION OF THE NEW VARIETY

Figure 1:
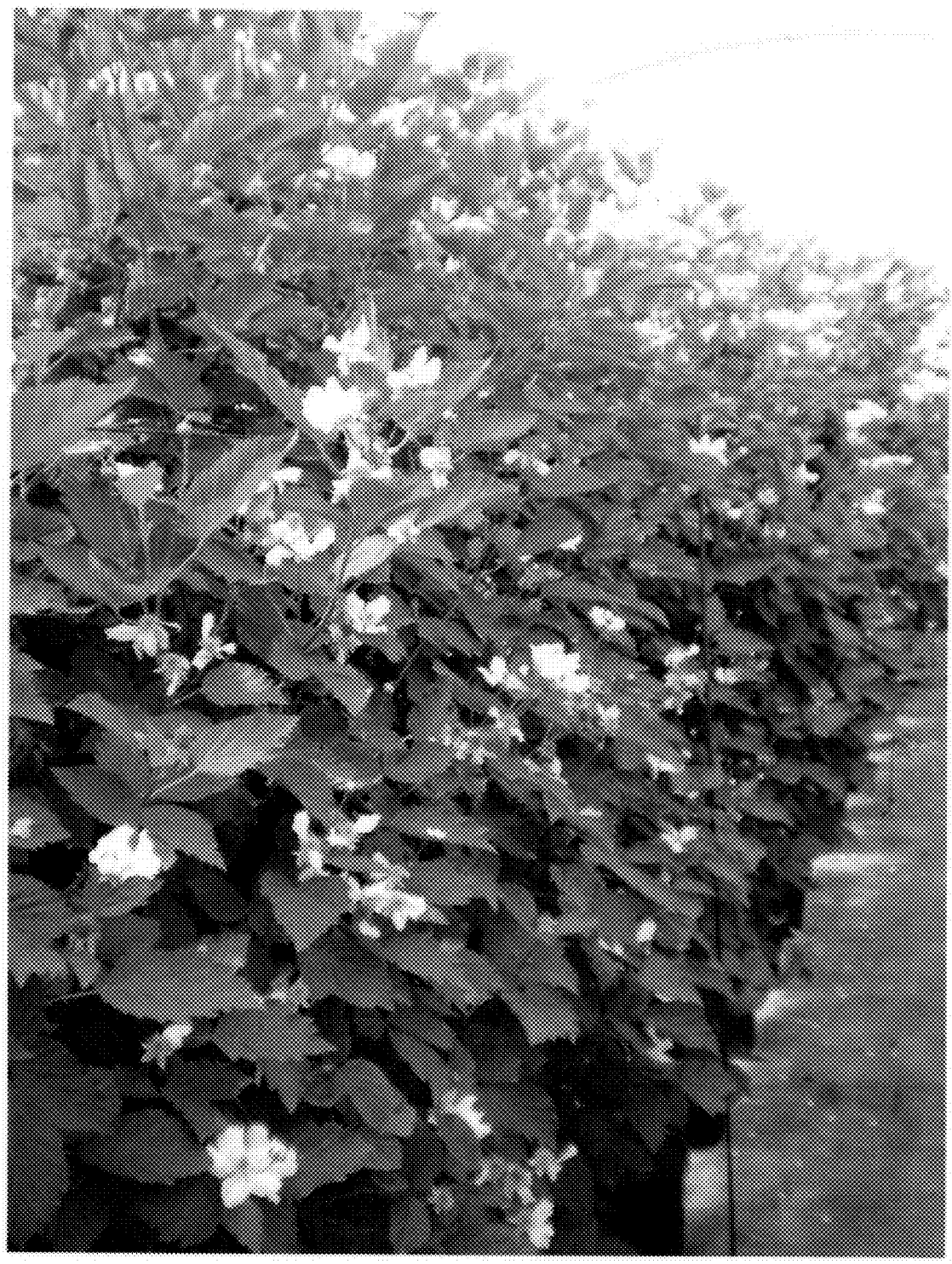
FIG. 1 shows the whole plant, including foliage and flowers.
Figure 2:
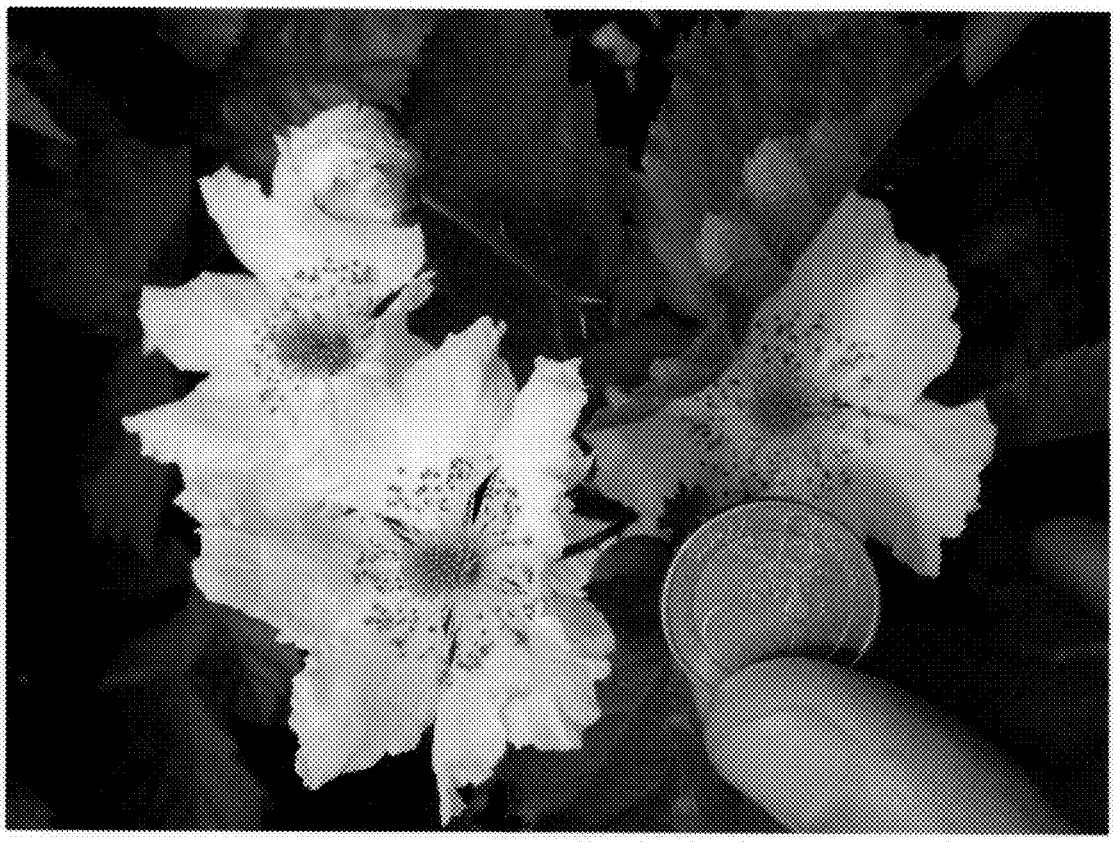
FIG. 2 shows a close-up of the flowers.
Figure 3:
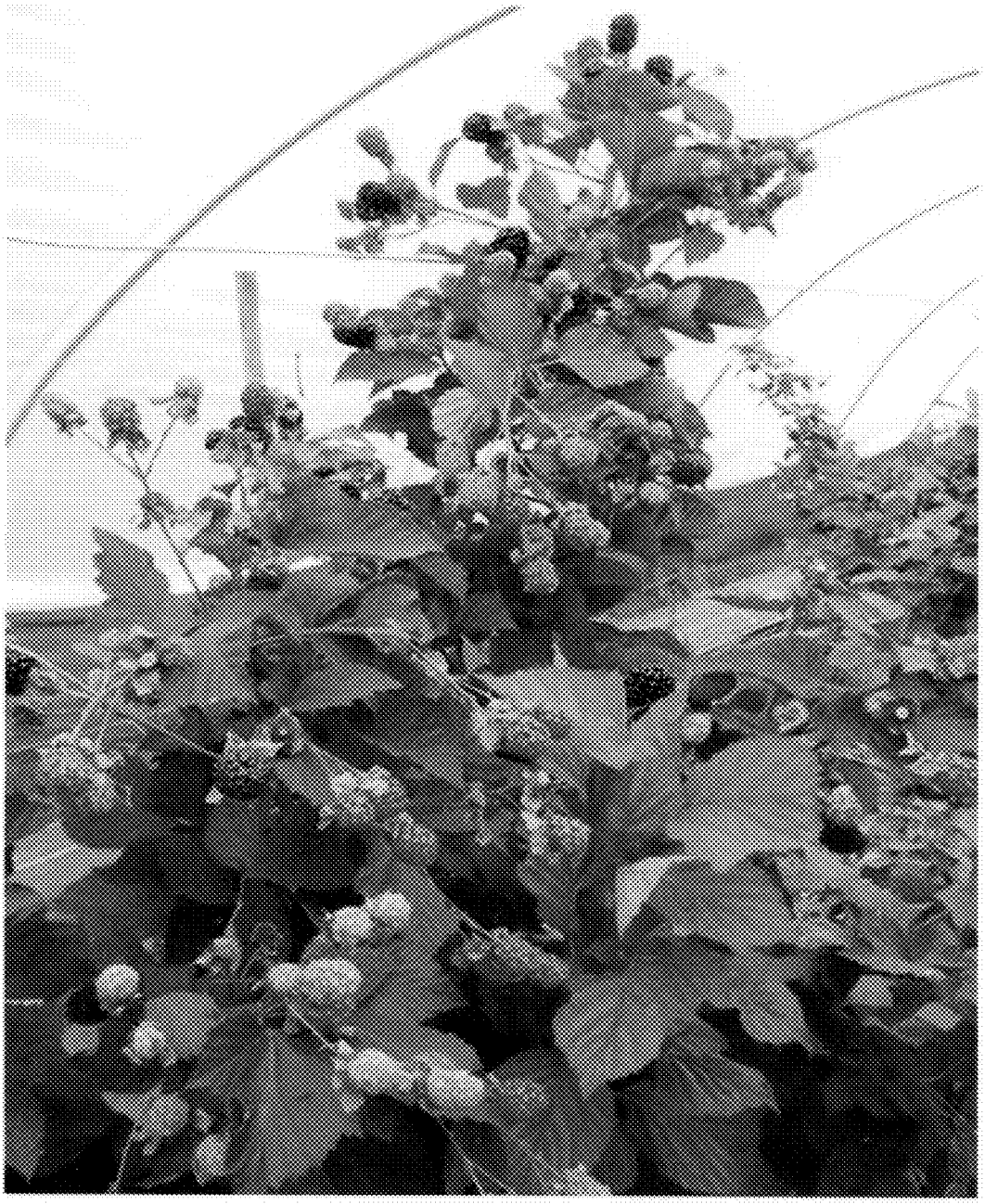
FIG. 3 shows a cane with both immature and mature berries.
Figure 4:
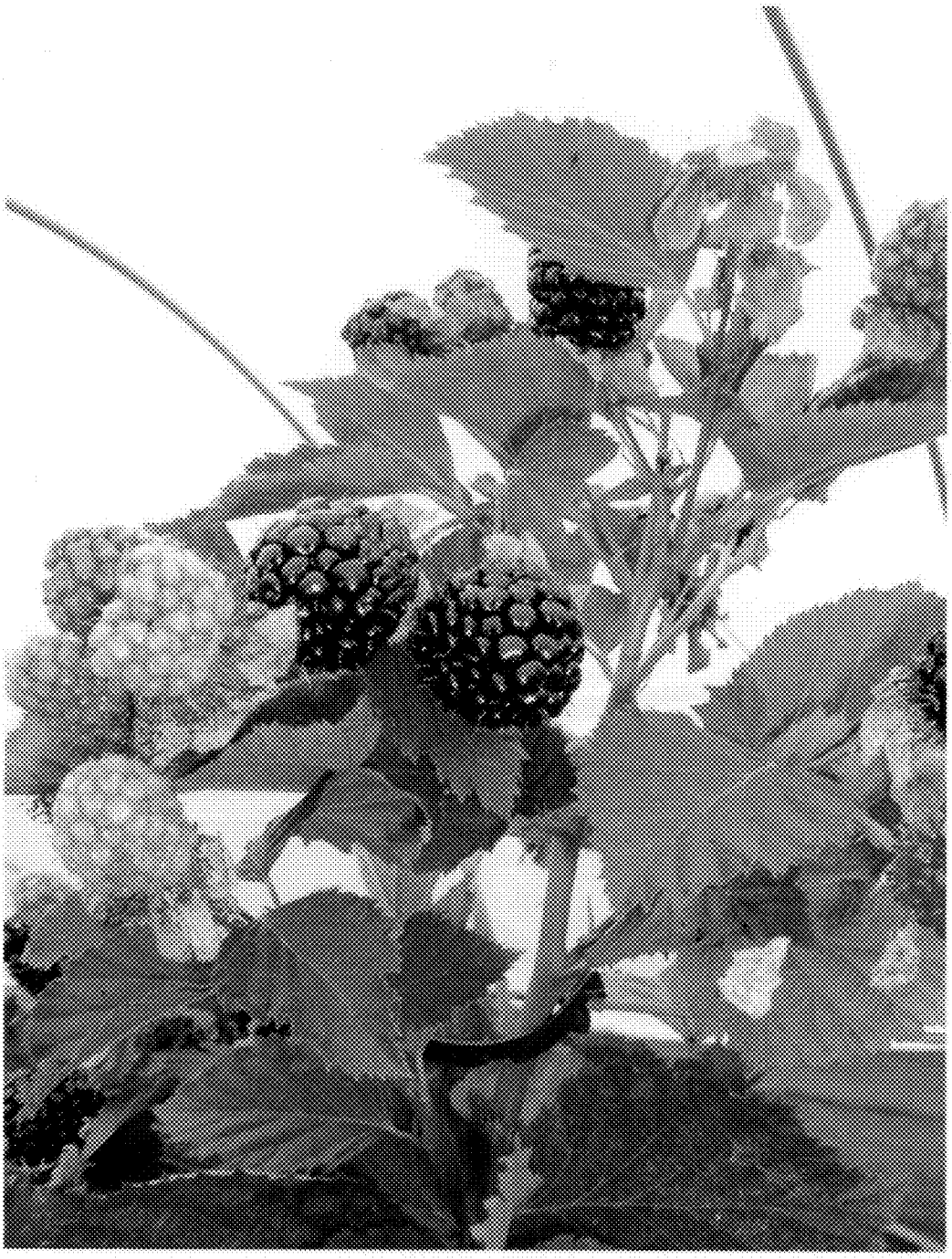
FIG. 4 shows a close-up of both immature and mature berries.

The following description of 'Reuben' is based on observations of two-year-old plants taken from 2006 to 2008 in Spalding, Lincs, United Kingdom. Description is in accordance with UPOV terminology. 'Reuben' has not been observed under all possible environmental conditions. Color terminology follows The Royal Horticultural Society Colour Chart, London (R.H.S.) (2001 edition).

DETAILED BOTANICAL DESCRIPTION

Classification:

*Family*.—Rosaceae.

*Botanical*.—*Rubus* subgenus *Eubatus* sect. *Moriferi & Ursini* hybrid.

*Common name*.—Blackberry.

*Variety name*.—'Reuben'.

Parentage:

*Female parent*.—The blackberry plant 'A-2292T' (unpatented).

*Male parent*.—The blackberry plant 'APF-44' (unpatented).

Plant:

*Vigor*.—Medium.

*Growth habit*.—Erect and compact.

*Productivity*.—High.

*Propagation*.—Tissue culture and root cuttings.

*Self-fruitfulness*.—Self-fertile.

Fruiting lateral:

*Lateral length*.—Medium.

*Length* (*4th lateral from tip*) *average* (*cm*).—7.5 cm.

*Width*.—5.0 mm to 7.0 mm.

*Number of fruit per lateral*.—Average: 10. Range: 8 to 12.

Shoot:

*Number of young shoots*.—6 to 8 per plant.

*Very young shoots intensity of anthocyanin coloration*.—Weak, RHS 41A.

*Time of young shoot emergence from soil* (*under normal conditions in the United Kingdom*).—April.

*Young shoot pigmentation*.—Medium-green, RHS 143B.

*Shoot length* (*cm*).—Average: 200. Range: 150 cm to 250 cm.

*Glaucosity* (*waxy bloom*) (*observed on full-grown shoot after picking*).—Present.

*Cane cross section* (*from mid cane observed at end of first growing season*).—Rounded.

*Mature primocanes*.—Diameter at base: 11.0 mm. Diameter at midpoint: 9.0 mm. Diameter at terminus: 4.0 mm. Internode length at base: 5.0 mm. Internode length at midpoint: 3.0 mm. Internode length at terminus: 1.5 mm. Thorn density/30 cm at base: 35. Thorn density/30 cm at midpoint: 18. Thorn density/30 cm at terminus: 15. Primocane color at base: RHS 137. Primocane color at midpoint: RHS 143B. Primocane color at terminus: Green.

*Dormant cane color*.—Pale-brown.

*Pubescence on canes*.—Few, downward.

Cane internodal distance (distance between nodes):

*Internodal distance* (*cm*) (*at central ⅓ of cane*).—Average: 6.0 cm. Range: 3.0 cm to 7.0 cm.

Leaves:

*Mature compound leaf length*.—16.7 cm.

*Mature compound leaf width*.—19.0 cm.

*Color*.—Base: Abaxial: RHS 137B. Adaxial: RHS 137C. Midpoint: Abaxial: RHS 137B. Adaxial: RHS 137A. Terminal: Abaxial: RHS 144B. Adaxial: Green.

*Arrangement*.—Palmate.

*Number of leaflets*.—5.

*Relief between veins*.—Weak.

*Glossiness*.—Medium.

*Cross section profile*.—V-shape.

*Petiole*.—Length (cm): Average: 3.0 cm. Range: 3.0 cm to 6.0 cm. Pigmentation of upper surface: Pale green. Pigmentation color of upper surface: RHS 143C. Pigmentation of lower surface: Pale green. Pigmentation color of lower surface: RHS 143C.

*Petiolule*.—Length: 1.7 cm. Color: RHS 144B.

*Terminal leaflet*.—Length: Average: 11.0 cm. Range: 9.0 cm to 14.5 cm. Width: Average: 9.5 cm. Range: 7.5 cm to 11.5 cm. Shape: Ovate. Apex: Acute. Margin: Serrate. Teeth length: 1.5 mm. Teeth width at base: 1.0 mm. Base: Obtuse. Pubescence: Absent.

*Stipule*.—Length: 1.0 mm. Width: 1.4 mm.

Inflorescence:

*Type*.—Elongated simple cyme.

*Time of flowering*.—August to November.

*Flower size*.—Large.

*Number of flowers per cluster*.—4.

*Flower diameter*.—Average: 6.1 cm. Range: 4.0 cm to 7.1 cm.

*Flower depth*.—18.0 mm.

*Diameter of calyx relative to corolla*.—2.1 cm.

*Flower number* (*at 3rd node from tip of lateral*).—Average: 5. Range: 4 to 8.

*Petal*.—Length: Average: 2.4 cm. Range: 2.1 cm to 2.4 cm. Width: Average: 1.7 cm. Range: 1.4 cm to 1.9 cm. Color: White. Upper surface: RHS NN155B. Lower surface: RHS N155A. Number per flower: 5. Shape: Oval. Margin: 2.4 cm. Apex: 13.0 mm. Base: 6.0 mm. Length/width ratio (observe on secondary flowers): 1.4:1.0 cm.

*Sepal*.—Number per flower: 5. Length: 8.0 mm. Width: 5.5 mm. Shape: Triangular. Apex: 2.0 mm. Color: Upper surface: RHS 147C. Lower surface: RHS 147B.

*Peduncle*.—Length: 1.4 cm. Color: Green.

*Pedicel*.—Length: 0.9 cm.

Fruit:

*Time of ripening*.—Late.

*Harvest interval*.—August to November.

*Length of harvest season*.—10 to 12 weeks.

*Color*.—Immature: RHS 203A. Maturing: RHS 203B. Mature: RHS 203C.

*Glossiness*.—Strong.

*Shape*.—Oblong, blocky.

*Length*.—Average: 2.7 cm. Range: 2.5 cm to 2.9 cm.

*Width*.—Average: 2.1 cm. Range: 1.8 cm to 2.3 cm.

*Ratio of length to width*.—1.28:1.0 cm.

*Weight* (*g/fruit*).—14.5.

*Soluble solids* (%) (*in Brix*).—11.5%.

*Number of druplets/fruit*.—45.

*Seed weight* (*average per* 100).—0.43 g.

*Firmness*.—Very firm.

*Yield*.—3.5 kg of fruit per plant.

COMPARISON WITH PARENTAL AND COMMERCIAL VARIETIES

'Reuben' differs from the female parent 'A-2292T' (unpatented) in that 'Reuben' is primocane fruiting, while 'A-2292T' is floricane fruiting. Additionally, 'Reuben' is larger fruited and has a fruit that weighs on average 14.5 g, while fruit of 'A-2292T' weighs on average 6.0 g. Furthermore, 'Reuben' is thorny, while 'A-2292T' is thornless.

'Reuben' differs from the male parent 'APF-44' (unpatented) in that 'Reuben' is more vigorous and taller in primocane height than 'APF-44'. Additionally, 'Reuben' has larger fruit size potential, with a fruit that weighs on average 14.5 g, while fruit of 'APF-44' weighs on average 8.0 g.

'Reuben' differs from the commercial variety blackberry plant named 'Natchez' (U.S. Plant Pat. No. 20,891) in that 'Reuben' has larger fruit that weighs on average 14.5 g, while the fruit of 'Natchez' averages 8.9 g to 9.4 g. In addition, the plants of 'Reuben' are thorny, while the plants of 'Natchez' are thornless.

I claim:

1. A new and distinct variety of blackberry plant as described and shown herein.

* * * * *